United States Patent [19]

Ellis et al.

[11] 4,126,937

[45] Nov. 28, 1978

[54] MATERIAL AND METHOD FOR INTRODUCING IONIC SILVER TO DENTAL PULP

[75] Inventors: Franklin H. Ellis; Edward A. Thibodeau, both of Rochester, N.Y.

[73] Assignees: Sybron Corporation; Eastman Dental Center, both of Rochester, N.Y.

[21] Appl. No.: 780,467

[22] Filed: Mar. 23, 1977

[51] Int. Cl.$^2$ ............................................. A61K 5/02
[52] U.S. Cl. ........................................ 32/15; 128/409
[58] Field of Search ............... 128/409, 419 R, 419 F, 128/172.1; 32/15

[56] References Cited

U.S. PATENT DOCUMENTS

| | | | |
|---|---|---|---|
| 2,069,112 | 1/1937 | Oppenheim | 128/409 |
| 4,027,393 | 6/1977 | Ellis | 32/40 R |

*Primary Examiner*—Robert Peshock
*Attorney, Agent, or Firm*—Theodore B. Roessel; J. Stephen Yeo

[57] ABSTRACT

A pulp cap mixture is prepared from silver particles and a dental cement such as polycarboxylate cement. Provision is made to apply low intensity direct current through the material placed in proximity to the pulp tissue. Ionic silver is released which provides anti-bacterial action.

2 Claims, 1 Drawing Figure

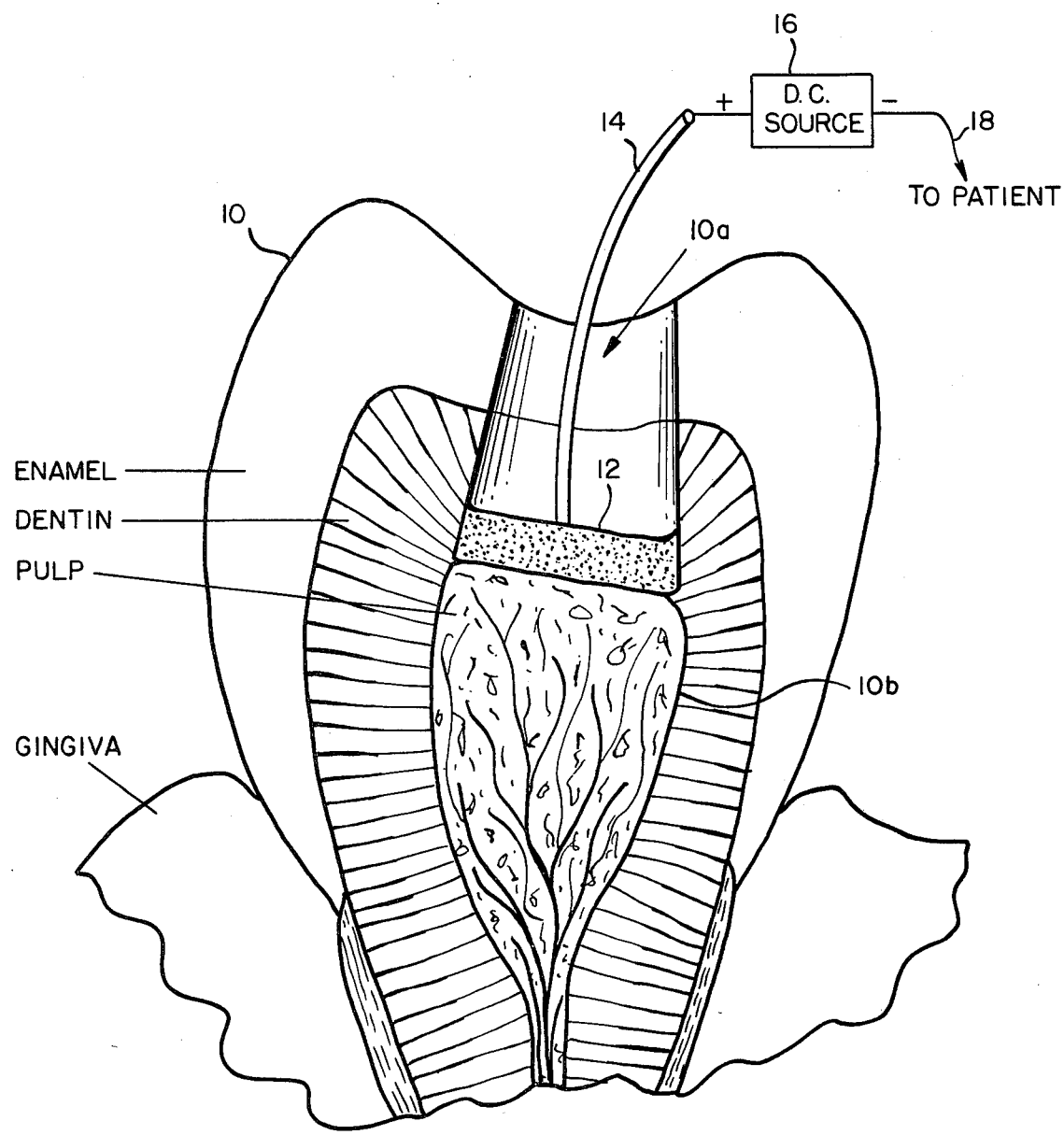

MATERIAL AND METHOD FOR INTRODUCING IONIC SILVER TO DENTAL PULP

BACKGROUND OF THE INVENTION

This invention concerns the treatment of dental pulp and tissue and more particularly is directed to treating pulp infections by electrical means.

Deep carious lesions present problems to the dentist if the bacteria which are always present in the mouth extend deep into the dentin. A worse situation exists if the bacterial infection extends through the dentin into the pulp. Pulpal tissue has limited blood supply so that systemic antibiotics are ineffective. Elimination of bacteria by topical antibiotics is also relatively ineffective because the antibiotic cannot penetrate deep enough into the tissue to reach all of the bacteria.

At the present time, calcium hydroxide is the most widely accepted agent for capping exposed pulp during treatment of deep caries. It is widely used as a liner near or directly in contact with the pulp, covered with another restorative material such as zinc oxide - eugenol paste. In most cases, the calcium hydroxide appears to promote formation of a secondary dentin bridge over the pulp. It is effective in the presence of infection if the amount of bacterial invasion is relatively small. However, even in cases where the treatment appears to be successful, there is often chronic inflamation of the soft tissue. Occasionally the pulp is totally destroyed or calcified by the effects of the calcium hydroxide.

An object of the present invention is to provide bactericidal affects to viable pulp (soft tissue) and dentin within a tooth that has become infected, thus possibly avoiding need for a root canal treatment which destroys the vitality of the tooth.

PRIOR ART

Applicants are aware of the following U.S. patents which pertain to electric dental treatment.

Oppenhein in U.S. Pat. No. 2,069,112 teaches, for insertion in a root canal, the use of an electric couple fashioned from gold and silver wire which may be left in after treatment. No external source is called for.

Kruse in U.S. Pat. No. 2,121,875 calls for precoating with silver compounds a silver bearing anode for insertion into a root canal. Continuous current is not called for but in situs reactivation may be required.

Meiman in U.S. Pat. No. 2,276,623 inserts a wire into a root canal and applies 0.5 to 1 milliamperes of negative current for sterilization of the area.

Moore U.S. Pat. No. 2,355,231 treats infected epithelial tissue such as pyorrha pockets by applying a positive potential to the area. A conductive jelly containing metal salts may be used. The desired result is the destruction of tissue.

Knappwost in U.S. Pat. No. 2,655,922 provides a cathode of silver-palladium alloy for the release of OH ions by gavanic action. A different metal is used for an anode.

Summers U.S. Pat. No. 3,019,787 applied ionized floride by means of 0.2 to 0.7 millamperes of positive direct current.

Ellis et al. describes in U.S. Pat. No. 3,964,477 a method of sterilizing skin tissue by using silver or silver bearing material as the positive electrode in a system utilizing low intensity direct current.

In U.S. Pat. No. 4,027,393 (Ser. No. 614,911, allowed) Ellis et al teach the use of a silver post for insertion into a root canal. Low intensity direct current releases ionic silver providing antibacterial action.

The above cited patents are the most relevant known to Applicants at the time of filing.

BRIEF DESCRIPTION OF THE DRAWING

FIG. 1 is a cross-section of a tooth undergoing therapeutic treatment following the practice of our invention.

SUMMARY OF THE INVENTION

A material for dental pulp caps is a mixture of silver particles suspended in a dental cement such as polycarboxylate. A mixture of polycarboxylate and 65 to 85% silver flakes is preferred.

The mixture may be used as a dental pulp cap. Direct current in the order to 1 to 40 microamperes is caused to flow through the cap releasing ionic silver into the surrounding tissue. For electrical contact a silver wire may be embedded in the pulp cap which current flows and then clipped flush.

DESCRIPTION OF THE PREFERRED EMBODIMENTS

Our invention calls for the use of silver particles mixed with a carrier for use as a dental pulp cap. With the application of direct current electricity, the silver provides antibacterial action for infected dentin and viable dental pulp.

FIG. 1 is schematic representation of a tooth which has been prepared for restoration by removing infected dentin leaving a cavity 10a.

Special dental cap material is prepared by mixing silver particles with a suitable carrier such as polycarboxylate dental cement, an example being the formulation sold under the trademark "Durelon".

The silver may be in the form of powder, precipitate, flakes or the like. We prefer silver flakes, 0.5 to 1 microns thick and 14 to 17 microns wide, as this form produces good results at low concentrations. Approximately 65% to 85% of the total weight of cap material is preferred, to assure conductivity and adhesion.

The polycarboxylate cement is available as a liquid and a powder to be mixed before use. The silver may be added to the powder or added after the powder is mixed with the liquid. After mixture, the resulting material remains soft and moldable for a few minutes.

During this time, a thin layer of our pulp cap material 12 is placed in the prepared cavity 10a on the pulp chamber 10b if exposed or on the dentin near the pulp chamber. The pulp cap material will act as a positive electrode and it is best if provision is made for electrical contact.

Accordingly, as an addition feature of our invention, a piece of silver wire 14 is embedded in the material while it is still soft and the material is then allowed to harden. After the material has hardened, positive direct current is caused to flow through the silver laden pulp cap material 12 causing bactericidal silver ions to be released into the tissue proximate to the material. Direct current is best supplied by a constant current source 16. A return path 18 must be provided from a contact on the patient (not shown) to the source so as to complete the electrical circuit. Direct current in the range of 1 to 40 microamperes is preferred, being applied for approximately ten minutes.

The silver wire 14 is then clipped flush with the surface of the material 12 and the dentist proceeds with the restoration of the tooth in his normal manner.

Silver ion activity continues for 3 or 4 hours at a slowly decreasing rate and then continues at a very low level indefinitely.

We claim:

1. The method of applying ionic silver to a tooth undergoing dental restoration comprising the steps of:
    preparing a cavity by removing infected dentin;
    applying a layer of a soft and moldable carrier mixed with silver particles, within said cavity and in proximity to the pulp chamber of said tooth said carrier being hardenable,
    allowing the carrier to harden; and
    causing positive direct in the range of 1 to 40 microamperes to flow through the layer into adjacent tissue for a time period.

2. The method of claim 1 which includes the further steps of inserting a silver wire into the layer before the carrier hardens, said wire providing electrical connection to the layer; and cutting the wire flush to the layer after completion of the application of direct current.

* * * * *